US00PP18236P2

(12) United States Plant Patent

Kaagman

(10) Patent No.: US PP18,236 P2
(45) Date of Patent: Nov. 20, 2007

(54) *CAMPANULA* PLANT NAMED 'CAMP BULE'

(50) Latin Name: ***Campanula* hybrid**
Varietal Denomination: Camp Bule

(75) Inventor: Pim Kaagman, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/413,989
(22) Filed: Apr. 28, 2006
(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

GTITM UPOVROM Citation for 'Camp Bule' as per QZ PBR 20050112; Jan. 24, 2005.*

* cited by examiner

*Primary Examiner*—Kent Bell
(74) *Attorney, Agent, or Firm*—Jondle & Associates, P.C.

(57) ABSTRACT

A new *campanula* plant particularly distinguished by small to medium-sized blue-violet, bell-shaped flowers, floriferous with the flowers borne well-above the foliage, an early flowering response, deep green and slightly glossy foliage with small, cordate leaves, a compact, well-branched growth habit and a mainly tight and bushy to later partly decumbent plant habit, is disclosed.

1 Drawing Sheet

Genus and species: *Campanula* hybrid.
Variety denomination: 'Camp Bule'.

BACKGROUND OF THE NEW PLANT

The present invention comprises a new and distinct cultivar of *campanula,* botanically known as *Campanula* hybrid, and hereinafter referred to by the cultivar name 'Camp Bule'. The new cultivar originated from a hybridization made in May 1995 in Andijk, The Netherlands. The female parent was 'CR-37-2', a proprietary (unpatented) interspecific blue-flowered *campanula* plant, while the male parent was 'CR-40-2', a proprietary (unpatented) interspecific blue-flowered *campanula* plant. The seeds produced by the hybridization were sown in February 1996, and the resulting seedlings were selected in July 1996. A single plant selection was chosen for further evaluation and for asexual propagation in 1997.

The new cultivar was created in 1995 in Andijk, The Netherlands and has been asexually reproduced repeatedly by vegetative cuttings and tissue in Andijk, The Netherlands over a nine-year period. 'Camp Bule' has also been trialed at Hillscheid, Germany. The present invention has been found to retain its distinctive characteristics through successive asexual propagations.

Plant Breeder's Rights for this cultivar were applied for in Canada on Mar. 21, 2006 and with the European Union on Jan. 24, 2005.

SUMMARY OF THE INVENTION

The following are the most outstanding and distinguishing characteristics of this new cultivar when grown under normal horticultural practices in Andijk, The Netherlands and Hillscheid, Germany.

1. Small to medium-sized blue-violet, bell-shaped flowers;
2. Floriferous with the flowers borne well-above the foliage;
3. An early flowering response;

4. Deep green and slightly glossy foliage with small, cordate leaves;
5. A compact, well-branched plant habit; and
6. A mainly tight and bushy, later partly decumbent growth habit.

DESCRIPTION OF PHOTOGRAPH

This new *campanula* plant is illustrated by the accompanying photograph which shows overall plant habit including blooms, buds, and foliage of the plant; the colors shown are as true as can be reasonably obtained by conventional photographic procedures. The photograph is of 5-month-old plants grown in a greenhouse in Andijk, The Netherlands in May 2003.

DESCRIPTION OF THE NEW CULTIVAR

The following detailed description sets forth the distinctive characteristics of 'Camp Bule'. The data which define these characteristics were collected from asexual reproductions carried out in Andijk, The Netherlands. The plant history was taken partly on 5-week old plants, still in a vegetative state and grown in Hillscheid, Germany. Rooted cuttings were planted in 10.5-cm pots and grown in a greenhouse. The plants were not pinched. Flower observations were made on 35-week-old plants in fall of 2005. Color readings were taken under natural light. Color references are primarily to The R.H.S. Colour Chart of The Royal Horticultural Society of London (R.H.S.) (2001).

DETAILED BOTANICAL DESCRIPTION

Classification:
*Family.*—Campanulaceae.
*Botanical.*—*Campanula* hybrid.
*Common name.*—Bellflower.

Parentage:
*Female parent.*—'CR-37-2', a proprietary interspecific blue-flowered *campanula* plant (unpatented).

*Male parent.*—'CR-40-2', a proprietary interspecific blue-flowered *campanula* plant (unpatented).

Growth:

*Form.*—Herbaceous perennial; continuously flowers under long-day conditions (late spring through early fall); for commercial purposes, the variety can be cultivated as an annual.

*Habit.*—Free-branching with many upright, flexible stems, tight and bushy, later partly decumbent plant habit.

*Height* (*measured from the top of the soil*).—10 cm.

*Width* (*horizontal plant diameter*).—12 cm.

*Propagation.*—Terminal tips for cutting.

*Time to produce a finished flowering plant.*—10 to 13 weeks for a 10 cm to 12 cm pot.

*Outdoor plant performance.*—Use in small containers or in flower borders.

*Time to initiate and develop roots.*—21 days.

*Root description.*—Fibrous and white.

Stems:

*Average number* (*per plant*).—15 to 17.

*Length.*—10 cm to 14 cm.

*Internode length.*—0.5 cm to 1.0 cm.

*Diameter* (*at midpoint*).—0.1 cm to 0.2 cm.

*Color.*—RHS 145A (light-green) at the midpoint and deeper, RHS 144B, near the tips.

*Anthocyanin.*—Occasionally RHS 174A near the base.

*Texture.*—Smooth and sparsely pubescent.

Leaves:

*Arrangement.*—Alternate.

*Size.*—Length (fully expanded): 2.0 cm. Width: 2.1 cm.

*Shape.*—Mostly cordate to nearly round.

*Margin.*—Somewhat serrate.

*Apex.*—Mainly obtuse.

*Base.*—Weakly cordate, nearly truncate.

*Color.*—Immature leaves: Upper surface: RHS 137C. Lower surface: RHS 137D. Mature leaves: General: Deep green. Upper surface: RHS 137A. Lower surface: RHS 137D.

*Texture.*—Glabrous and weakly glossy.

*Venation.*—Between palmate and pinnate.

*Venation color.*—RHS 144D for the midrib, lower surface.

*Petioles.*—Length: 1.0 cm to 2.3 cm. Width: 0.1 cm to 0.2 cm. Color: Upper surface: RHS 137D. Lower surface: RHS 145A. Texture: Smooth with a few short hairs.

Flower bud:

*Shape.*—Narrow and oval (elongated) with deep furrows.

*Size.*—Length: 1.3 cm. Diameter: 0.6 cm.

*Color at tight bud.*—RHS 92A (light-blue) at the tip; RHS 92D for the rest of the bud.

Inflorescence:

*Blooming habit.*—Continuous under long-day conditions.

*Inflorescence type.*—Peduncles emerge from the leaf axils of the upper nodes and inflorescence is mostly upright directed.

*Number of flowers per inflorescence.*—About 2 to 5 flowers and buds.

*Lastingness of individual blooms on the plant.*—About 14 days.

*Fragrance.*—None.

*Length.*—8.0 cm to 9.0 cm.

*Diameter.*—3.0 cm to 4.0 cm.

*Peduncel.*—Length: Up to 8 cm. Diameter: 0.1 cm to 0.2 cm. Color: RHS 143B (green). Texture: Glabrous.

*Pedicels.*—Length: 1.0 cm to 3.0 cm. Diameter: 0.1 cm. Color: RHS 143A (green). Anthocyanin: Absent. Texture: Glabrous.

Flowers:

*Flower type.*—Solitary, round (actinomorphic) and campanulate.

*Corolla.*—Shape: Bell-shaped with somewhat pointed lobes; composed of 5 petals that are mainly fused and open slightly outwards. Size: Diameter: 2.5 cm. Depth: 1.4 cm. Color: General: Violet-blue. Outer surface: RHS 92A. Inner surface: RHS 91A.

*Petals.*—Size (from the opening): Length: 0.8 cm. Width: 1.0 cm. Quantity: 5. Apex: Acute to obtuse. Base: Fused. Margin: Entire. Texture: Glabrous.

*Calyx.*—Composed of 5 sepals fused at the base.

*Sepals.*—Number: 5. Color: Upper surface: RHS 137A to RHS 139A (deep green). Lower surface: RHS 137A. Length: 0.4 cm. Width: 0.1 cm at the base. Shape: Narrow, lanceolate, reflexed. Apex: Acute. Base: Fused. Margin: Mostly entire, occasionally single notches. Texture: Glabrous, glossy.

Reproductive organs:

*Stamens.*—Quantity: 5 and upward-directed; close to the lower part of the style. Filament: Color: RHS N155D (white). Length: 0.3 cm to 0.4 cm. Diameter: 0.3 cm to 0.4 cm at the base and 0.1 cm under the stamen. Anther: Color: RHS N187A. Size: Length: 0.2 cm to 0.3 cm. Diameter: Less than 0.1 cm. Pollen: Color: RHS 162D (yellowish). Amount: Moderate.

*Pistil.*—Quantity: 1. Length: 1.7 cm. Stigma: Color: RHS 157D (palest green-white). Shape: 3-lobed with brush-like-arranged hair below the stigma. Style: Color: RHS N155A (whitish) at the lower part and RHS 92B (light-blue) at the upper part. Length: 1.2 cm to 1.3 cm.

*Ovary.*—Type: Intermediate (neither superior nor inferior). Shape: Ovate. Length: 0.4 cm to 0.5 cm. Diameter: 0.3 cm. Color: RHS 145A (pale green).

Fruit and seed set: None observed.

Disease and insect resistance: No special observations made.

COMPARISON WITH PARENTAL AND COMMERCIAL CULTIVARS

'Camp Bule' differs from the female parent 'CR-37-2' (unpatented) in that 'Camp Bule' has smaller bell-shaped flowers, while 'CR-37-2' has cup-shaped flowers. Additionally, 'Camp Bule' has a lighter flower color and smaller leaves than 'CR-37-2'.

'Camp Bule' differs from the male parent 'CR-40-2' (unpatented) in that 'Camp Bule' has larger and deeper blue flowers than 'CR-40-2'.

'Camp Bule' differs from the commercial variety 'Bavaria Blue' (unpatented) in that 'Camp Bule' has larger, deeper-blue flowers than 'Bavaria Blue'.

I claim:

1. A new and distinct cultivar of *campanula* plant as shown and described herein.

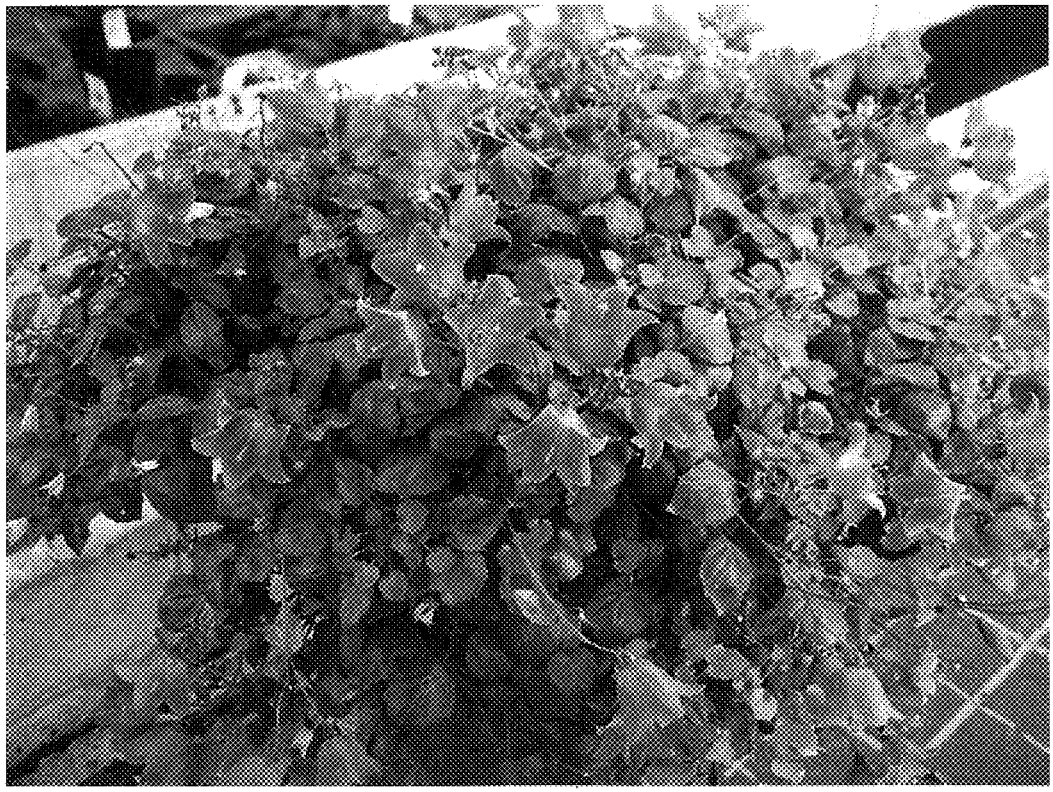

* * * * *